United States Patent
Yanof et al.

[19]

[11] Patent Number: 6,035,228

[45] Date of Patent: *Mar. 7, 2000

[54] FRAMELESS STEREOTACTIC ARM APPARATUS AND METHOD OF USING SAME

[75] Inventors: Jeffrey H. Yanof, Solon; Ronald B. Sharpless, S. Euclid; David Jeri, Parma; Christopher Bauer, Westlake; Daniel S. Furst, Concorde, all of Ohio

[73] Assignee: Picker International, Inc., Highland Heights, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/980,443

[22] Filed: Nov. 28, 1997

[51] Int. Cl.[7] ........................................................ A61B 5/00
[52] U.S. Cl. ............................................ 600/429; 606/130
[58] Field of Search ................................... 395/80, 93, 94; 606/130; 600/429, 407, 427, 411, 417, 414, 426

[56] References Cited

U.S. PATENT DOCUMENTS

| | | | |
|---|---|---|---|
| 4,791,934 | 12/1988 | Brunnett | 128/653 |
| 5,078,140 | 1/1992 | Kwoh | 128/653.1 |
| 5,099,846 | 3/1992 | Hardy | 128/653.1 |
| 5,142,930 | 9/1992 | Allen et al. | 74/469 |
| 5,229,288 | 7/1993 | Glassman et al. | 395/80 |
| 5,230,338 | 7/1993 | Allen et al. | 128/653 |
| 5,309,913 | 5/1994 | Kormos et al. | 128/653.1 |
| 5,398,684 | 3/1995 | Hardy | 128/653.1 |
| 5,427,097 | 6/1995 | Depp | 128/653.1 |
| 5,524,180 | 6/1996 | Wang et al. | 600/118 |
| 5,533,082 | 7/1996 | Grönemeyer et al. | 378/20 |
| 5,590,655 | 1/1997 | Hussman | 128/653.1 |
| 5,598,269 | 1/1997 | Kitaevich et al. | 356/399 |
| 5,622,170 | 4/1997 | Schulz | 128/653.1 |
| 5,628,327 | 5/1997 | Unger et al. | 128/749 |
| 5,647,373 | 7/1997 | Paltieli | 128/749 |
| 5,657,429 | 8/1997 | Wang et al. | 395/86 |
| 5,749,362 | 5/1998 | Funda et al. | 128/653.1 |
| 5,769,078 | 6/1998 | Kliegis | 128/653.1 |
| 5,807,377 | 9/1998 | Madhani et al. | 606/1 |
| 5,824,007 | 10/1998 | Faraz et al. | 606/130 |
| 5,868,675 | 2/1999 | Henrion et al. | 600/424 |

*Primary Examiner*—Ruth S. Smith
*Attorney, Agent, or Firm*—Fay, Sharpe, Fagan, Minnich & McKee, LLP

[57] ABSTRACT

An imaging apparatus (18) includes a frameless stereotactic arm apparatus (30) including a first base portion (42) mounted in a fixed relationship to the imaging device. A second free end (40) of the arm assembly is adapted to move into varied positions near a specimen disposed on the imaging apparatus. At least one pivot joint (44, 48, 52, 56, 60) is provided between the first base portion and the free end of the arm for permitting selective relevant movement between the arm members. Electro-mechanical and electromagnetic brake devices are provided at respective joints to selectively lock the free end of the arm assembly to the base portion. The brakes are responsive to a brake command signal (210) generated by the imaging device. A low pass filter (240) conditions the brake command signal to substantially eliminate high frequency electromagnetic switching noise in the stereotactic arm. So that the arm is movable in emergency situations, the brakes are adapted to rebase in response to application of a force in excess of a predetermined breakaway threshold force.

23 Claims, 8 Drawing Sheets

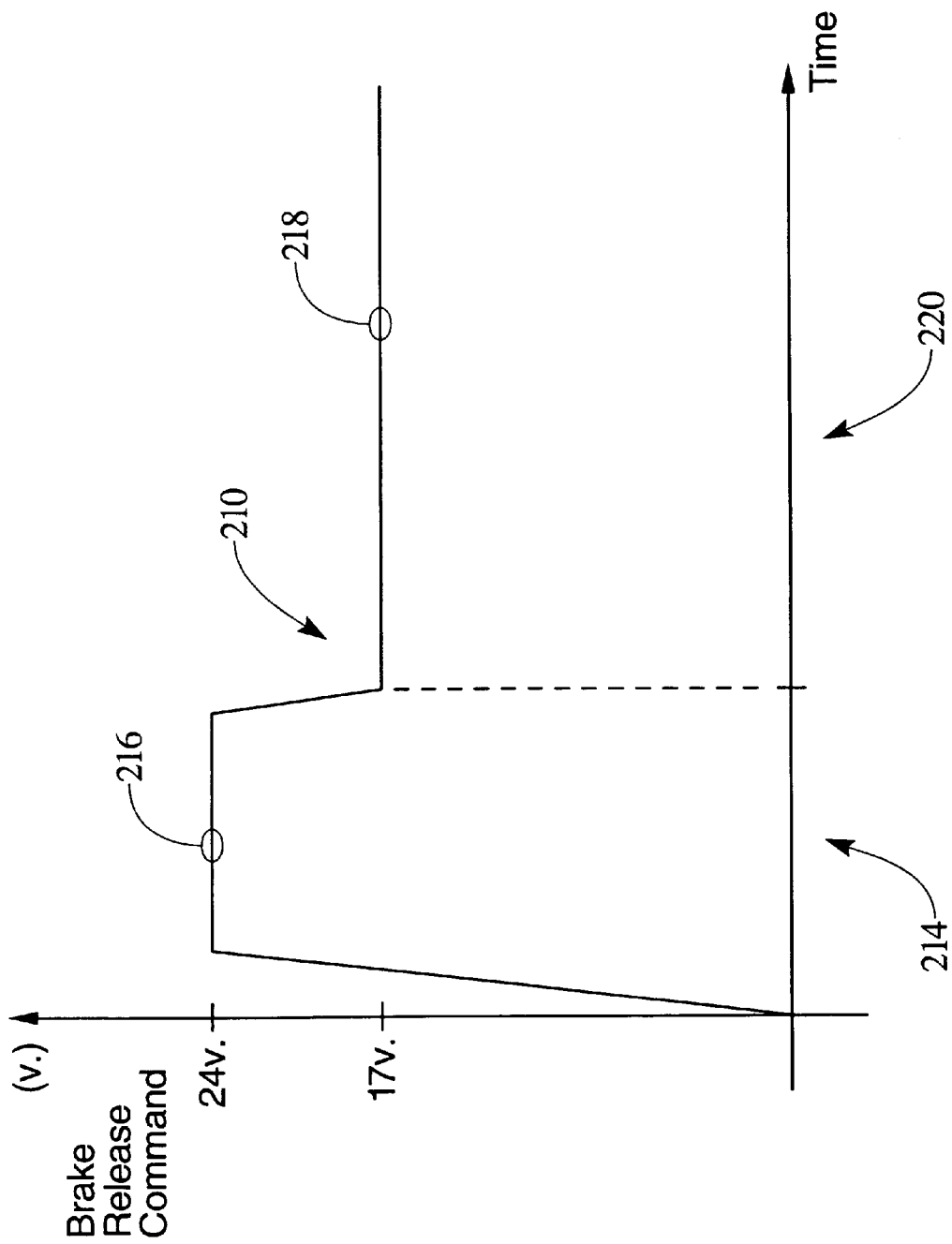

FRAMELESS STEREOTACTIC ARM APPARATUS AND METHOD OF USING SAME

BACKGROUND OF THE INVENTION

The present invention relates to the art of interactive image-guided surgery. It finds particular application in conjunction with stereotactic surgery performed in CT imaging systems using a frameless mechanical arm to guide minimally invasive surgical tools and will be described with particular reference thereto. It is to be appreciated, however, that the invention is also applicable to robotic and other mechanical arm mechanisms used as frameless guidance assist devices in other imaging systems including ultrasonic and magnetic resonance imaging (MRI) devices.

Heretofore, several mechanical arm type mechanisms have been proposed in interactive imaging systems for guiding intervertional surgical tools to allow accurate placement of catheters, drainage tubes, biopsy probes, or the like, within a patient's body. U.S. Pat. No. 5,142,930 teaches a mechanical arm having a fixed base at a first end and a tool holder on the other end. The tool holder is adapted to hold and guide interventional surgical tools. The mechanical arm is associated with a computer coupled to a display device displaying one or more images from an image space of a patient's anatomy generated by an imaging device. The computer tracks the location of the surgical tool through physical space, performs a transforming rotation of the physical space to the image space, and causes the display device to show the location of the surgical tool within the image space. Optical encoders are arranged at each gimbal joint of the mechanical arm in order to detect rotational or angular movement of the arm segments for accurate tracking of the end tip of a tool relative to the position of fiducial implants disposed in or on the patient.

One disadvantage of the above system, however, is the need for a bulky stereotactic localization frame. Although the position of a tool carried on the arm relative to the base is accurately tracked, the use of fiducial implants remains necessary to initialize a mapping between the internal coordinate system of the surgical image and the external coordinate system of the mechanical arm. In addition, the arm described in the system identified above is allegedly easy to manipulate and use because the arm is counterbalanced using conventional weight balancing techniques.

A frameless stereotactic arm apparatus that does not rely upon the bulky localization frame or the fiducial implants placed on a patient would reduce the setup time spent before surgery. It would be desirable to provide a frameless stereotactic arm apparatus with multiple arm segments which are lockable into fixed locations so that precise orientation and accurate guidance of surgical instruments is possible. Preferably, the lockable frameless stereotactic arm apparatus would include frictional brakes at each movable joint for locking the arm into any desired conformation against the force of gravity, but which would permit movement of the arm in emergency situations in response to application of a force in excess of a predetermined breakaway threshold force.

U.S. Pat. No. 5,078,140 teaches a jointed robotic arm useful in precisely orienting surgical tools and other implements used in conducting stereotactic surgery or other related procedures on human body parts. The mechanical arm used in this system includes six rotatable joints and a set of servo motors for moving the arm into predetermined orientations. The servo motors include electromagnetic brakes that are activated whenever power is removed from the robotic arm. Further, all of the servo motors incorporate optical incremental encoders that provide position and velocity feedback to the servo system driving the arm into the above-noted predetermined orientations. A specialized computer program with control software continuously monitors the angles and positions between all of the joints of the arm in relation to each other and in relation to a base member which is affixed to a metal ring member of a head frame fixed to a patient's head. The robotic arm includes a "free" mode which is useful for decoupling the servo motors from active servo control so that the arm may be manually manipulated.

One disadvantage, however, of the above stereotactic surgical system is that the mechanical arm must necessarily be connected to a rigid frame apparatus supported by the scanning table and attached to a relatively immovable body part of a patient, usually the head. The frame is bulky and often interferes with access to some parts of the patient's anatomy. It would, therefore, be desirable to provide a frameless stereotactic arm apparatus connected from overhead directly to an imaging apparatus rather than to a patient's head or to a stereotactic head frame, or the like.

The present invention provides a new and improved frameless stereotactic arm apparatus and method of using same for planning and executing image guided interventional procedures which overcomes the above-referenced problems and others.

SUMMARY OF THE INVENTION

In accordance with one aspect of the present invention, a frameless stereotactic surgical apparatus is provided. The apparatus includes an imaging device generating image information regarding a specimen disposed adjacent the imaging device. The frameless surgical apparatus further includes a mechanical arm assembly having a first base portion mounted in a fixed relationship to the imaging device. A second free end of the mechanical arm assembly is adapted to move into varied positions near the specimen on the imaging device. At least one pivot joint is provided between the base portion of the mechanical arm assembly and the second free end thereof for permitting selective relevant movement between the first base portion of the arm assembly and the second free end. A brake device adapted to selectively lock the first base portion to the second free end is provided. The brake device is responsive to a brake command signal generated by a control circuit associated with the imaging device. The function of the brake device and the logic for brake command signals operate in a fail safe mode such that a logical "1" on the brake command signal causes the brake device to rebase thereby movement of the stereotactic arm. In an absence of the brake command signal, a logical "0", the brake devices engage to lock the arm in place. This is advantageous during power failures or the like.

In accordance with yet another aspect of the present invention, the stereotactic arm is formed of multiple arm segments connected at a set of lockable joints. Each of the joints include a brake device for locking the multiple arm segments into position. In the preferred embodiment, all of the brakes operate in unison.

In accordance with a further aspect of the present invention, the amount of force holding the multiple arm segments in place is selectable by an interventionist so that the freedom of movement of the arm can be controlled. Some interventionists prefer stereotactic arms that are somewhat stiff and require a significant amount of effort to move into position. Other prefer a more relaxed arm that is less stiff and relatively easy to move into position.

In accordance with another aspect of the present invention, the frameless stereotactic surgical apparatus includes a position feedback device generating joint position signals indicating an orientation of the second free end of the mechanical arm assembly relative to the base portion thereof.

Still further, according to yet another aspect of the present invention, the first joint position signal is joint position signal information in arm space coordinates relating the mechanical arm assembly to the imaging device. The first image information regarding the specimen is image information in scanner space coordinates relating the specimen to the imaging device.

According to still yet another aspect of the present invention, a transform processor is provided for mapping a position of the free end of the mechanical arm in the arm space coordinates to a position in the scanner space coordinates.

In yet another aspect of the present invention, the brake command signal is generated at a first level for a first predetermined time period and, subsequently, at a second level for a second predetermined time period.

In yet another aspect of the present invention, the brake device is adapted to permit movement of the mechanical arm assembly from the predetermined fixed position in response to application of a first offsetting force applied to the mechanical arm in excess of a breakaway threshold force slightly greater than the gravitational force acting on the arm so that the arm is movable in emergency situations.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein:

FIG. 9 is a representative plot of a brake command signal generated by the imaging apparatus shown in FIG. 1; and, FIG. 10 is a schematic illustration of a brake controller used to generate the signal shown in FIG. 9 for locking the frameless stereotactic arm of FIG. 2 in predetermined fixed orientations.

DETAILED DESCRIPTION OF THE PREFERRED EMBODIMENT

Figure 1:
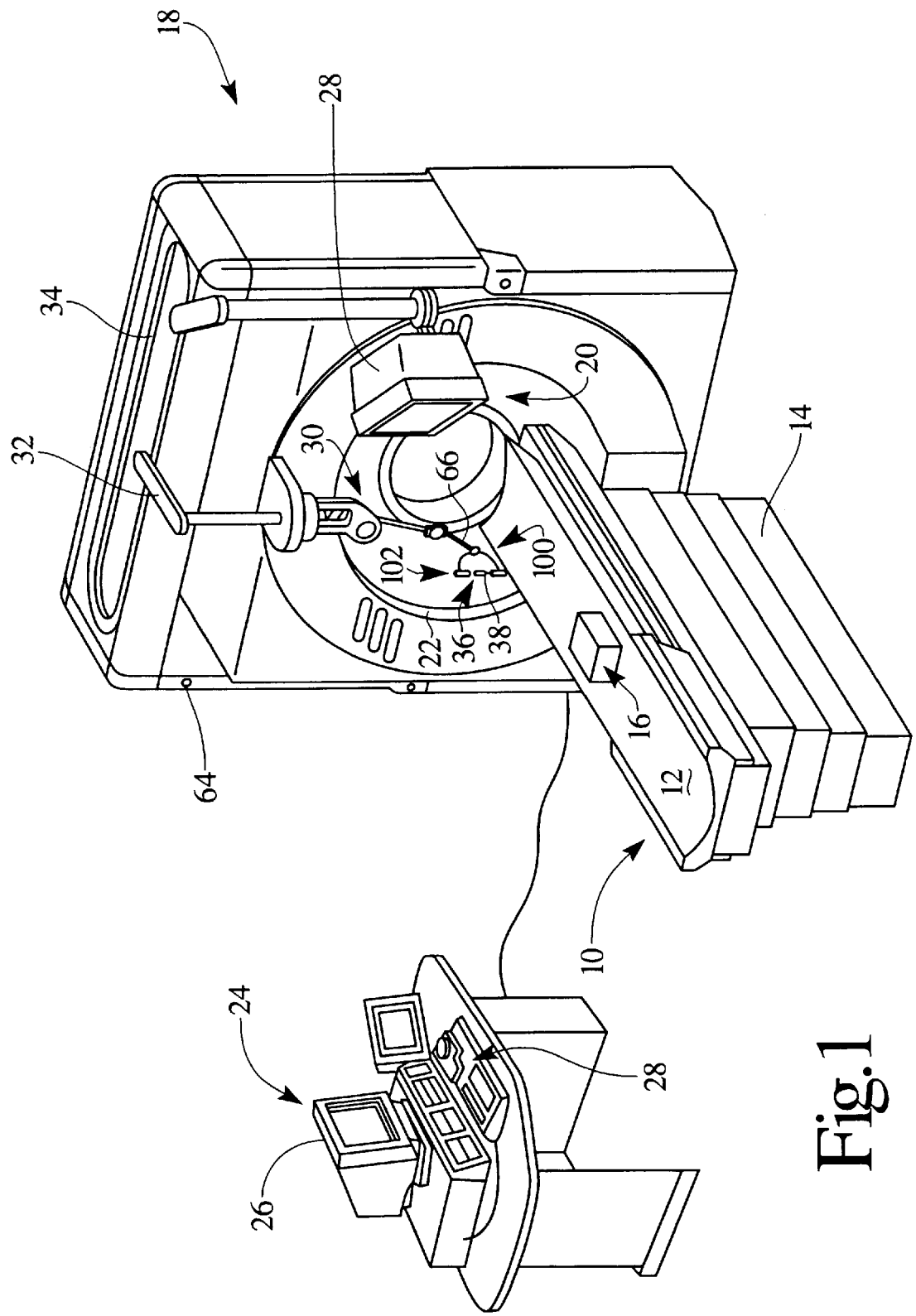
FIG. 1 is a diagrammatic illustration of a CT scanner with a frameless stereotactic arm apparatus for guiding surgical instruments in accordance with the present invention.

Referring now to the drawings wherein the showings are for the purposes of illustrating the preferred embodiments of the invention only and not for purposes of limiting same, with reference first to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration marker 16 disposed at a known, fixed location.

A planning, preferably volumetric diagnostic imaging apparatus 18 is disposed in axial alignment with the patient table such that a patient or subject on the patient support surface 12 can be moved into and through a bore 20 of the volumetric imager. In the illustrated embodiment, the volumetric imager is a CT scanner which includes an X-ray tube mounted for repeated circular travel within a preselected plane. The X-ray tube projects a fan-shaped beam of radiation through a ring 22 of radiation translucent material, through the patient support 12, through a region of interest of the subject, and to a ring or arc of radiation detectors positioned opposite the X-ray tube. As the X-ray tube rotates within the plane, a series of data lines are generated, which data lines are reconstructed into at least a slice image by a reconstruction processor included in a control console 26. The control console is typically remotely located in a shielded room adjacent the scan room containing the imaging apparatus 18. More specifically to the preferred embodiment, the patient support 12 moves longitudinally as the X-ray tube is rotating around the subject such that a selected volume of the patient is scanned along a spiral path or a series of slices. The position of the X-ray tube is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices, such as a keyboard, trackball, mouse, or the like. An interventional control console 28 is supported from overhead on a track atop the CT scanner as shown.

A mechanical frameless stereotactic arm assembly 30 is supported from overhead by a support arm 32 movable on an oval track system 34 affixed to the top of the volumetric diagnostic imaging apparatus 20 as generally shown. The gantry is preferably lockable in one or more predetermined fixed locations on the oval track so that a minimally invasive surgical instrument 36 carried on an interchangeable surgical instrument guidance device 100 formed in accordance with the present invention can be positioned in monitored positions and orientations by an interventionist in preparation for and in carrying out a surgical procedure. The surgical instrument illustrated in the FIGURE includes a biopsy needle 38 carried by a combined laser and cannula guidance device 102 formed in accordance with a first preferred embodiment of the present invention which will be described below. Overall, however, the position and orientation of the guidance device and the surgical instrument carried thereon are determined by the position of the mechanical arm assembly 30 and the location of the support arm 32 on the oval track system 34.

Figure 2:
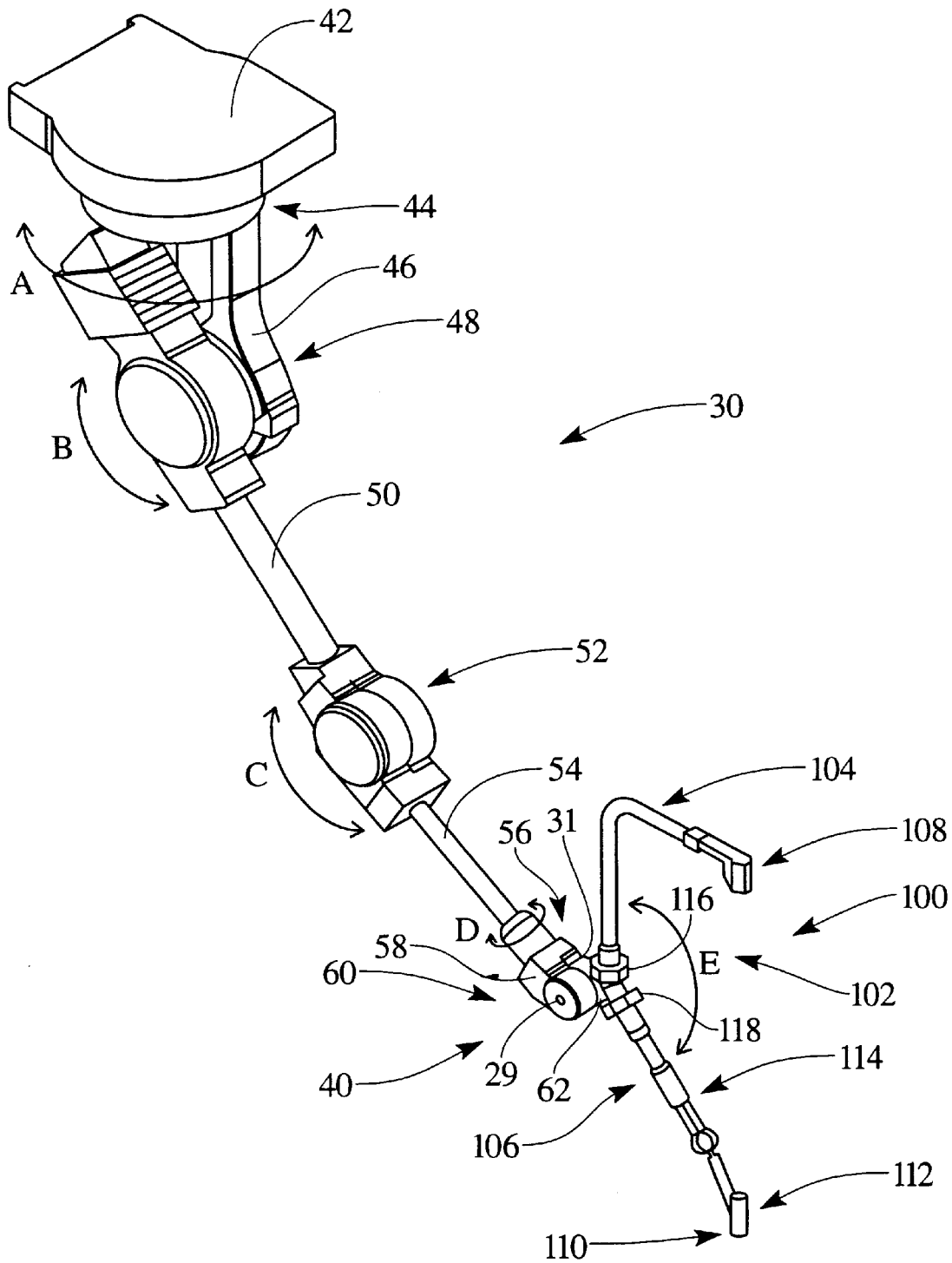
FIG. 2 is a perspective view of the frameless mechanical arm assembly carrying a guidance device formed in accordance with the present invention.

The frameless stereotactic arm assembly 30 is shown generally in FIG. 2 and includes a plurality of arm segments which are interconnected by pivot members forming joints between the arm segments. In that way, a free end 40 of the arm is selectively movable in multiple orientations as necessary to position the surgical instrument 36 into various desired positions over the patient support 12. A base member 42 is rigidly connected to the support arm 32 using suitable fasteners, epoxies, or the like. A base joint 44 permits rotation of a primary support member 46 in a direction marked A. Similarly, from the immovable base end of the arm, a shoulder joint 48 permits rotation of an upper arm member 50 in a direction marked B, an elbow joint 52 permits rotation of a lower arm member 54 in a direction marked C, a forearm joint 56 permits rotation of a knuckle member 58 in a direction marked D, and, lastly, a wrist joint 60 permits rotation of a wrist member 62 in a direction marked E.

In accordance with the present invention, at least one position resolver and one electro-magnetic brake, preferably an optical incremental encoder and friction brake respectively, are provided at each joint of the mechanical arm assembly 30 to monitor increment articulation and rotation of the arms relative to each other and to selectively lock the arm in place. The optical incremental encoders generate feedback pulses indicative of the movement and relative position of the various arm members in a well known manner. The feedback pulses are carried back to an imaging apparatus control circuit using suitable wires or flexible shielded cables extending through the multiple members of the arm assembly. In that way, the position and orientation of the wrist member 62 with respect to the imaging apparatus reference frame and the volumetric image representation are obtained by the imaging apparatus.

Further, in accordance with the present invention, a pair of membrane switches 29, 31 are provided on opposite sides of the wrist member 62. The membrane switches provide a very convenient way for an interventionist to simultaneously unlock the respective mechanical joints of the arm and position the surgical instrument guidance device 100 at various orientations. The membrane switches are connected through the mechanical arm to the control circuit illustrated in FIG. 10. One major advantage of placing the membrane switches onto opposite sides of the wrist member is that their location there enables the interventionist to use only one hand for both locking and unlocking the mechanical arm and, further for locating the free end thereof, while the arm is unlocked, into the desired position. As an alternative to the pair of membrane switches, however, other suitable toggle buttons, foot switches, or voice recognition systems could equivalently be used. However, the pair of opposing membrane switches are preferred because their position and orientation ensures that the interventionist has a firm grasp of the end of the arm as the brake release in response to the dual actuation of the switches. The interventionist must squeeze the switches together to rebase the brakes. Thus, the interventionist needs only to use one hand to hold the arm, locate the wrist of the arm in to position and selectively lock and unlock the brakes as necessary.

The position and orientation of surgical instruments carried by the arm assembly relative to the imaging apparatus reference frame and the volumetric image representation obtained by the imaging apparatus are resolved by providing interchangeable surgical instrument guidance devices 100 having a unique identification signal. The identification signal is used by the imaging apparatus control circuit to index a look up table for retrieving various physical dimensional and other functional parameters corresponding to the one or more guidance devices connected to the wrist member 62. In this manner, the physical dimension and other functional parameters, together with the mechanical interconnection which is measured by the resolvers and encoders, provides an accurate indication of the position and orientation of the guidance device 100 relative to the CT scanner and, hence, relative to the image acquired by the CT scanner.

Figure 3:
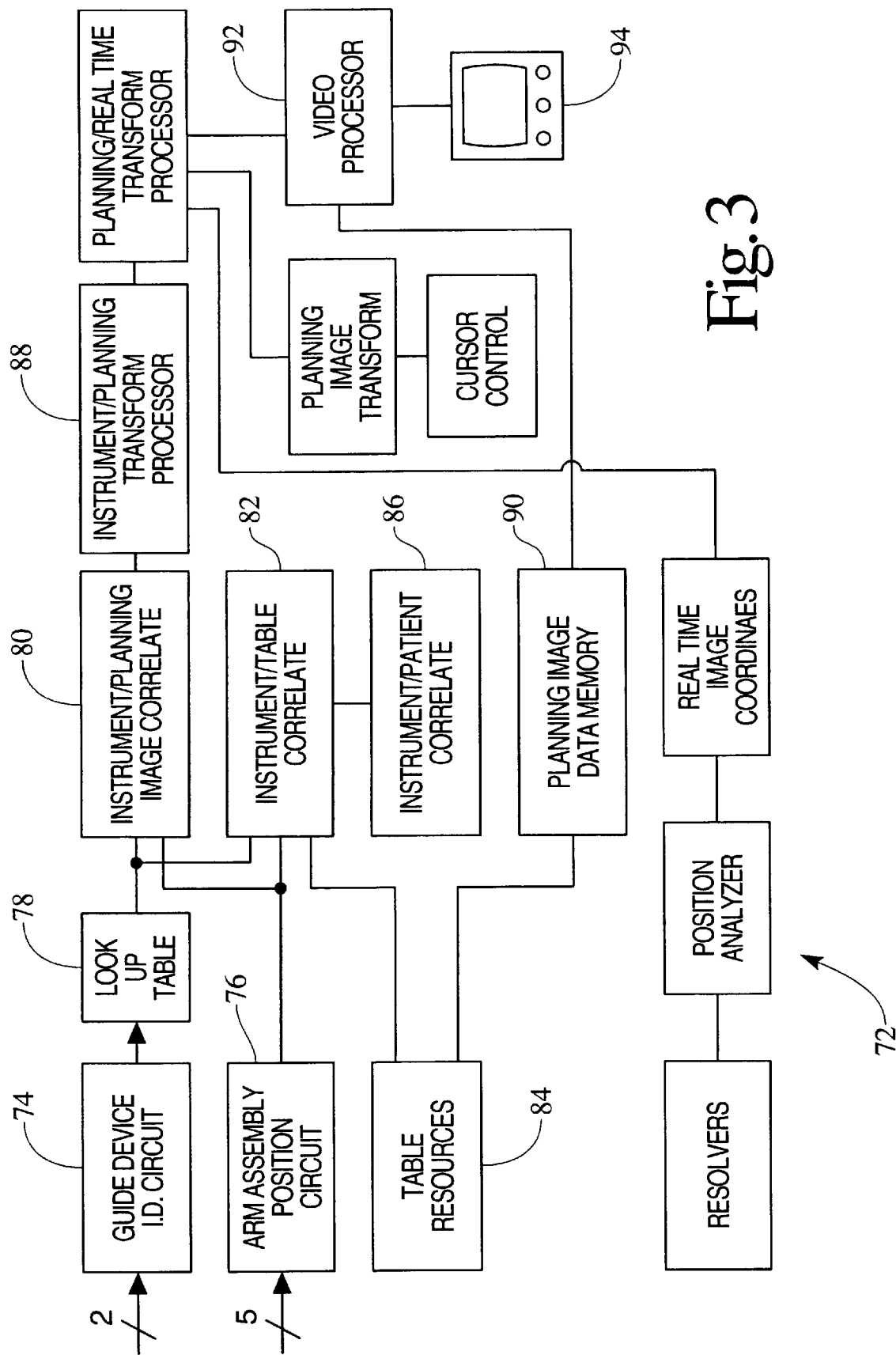
FIG. 3 is a diagrammatic illustration of the planning image processing performed with the apparatus of FIG. 1.
Figure 4:
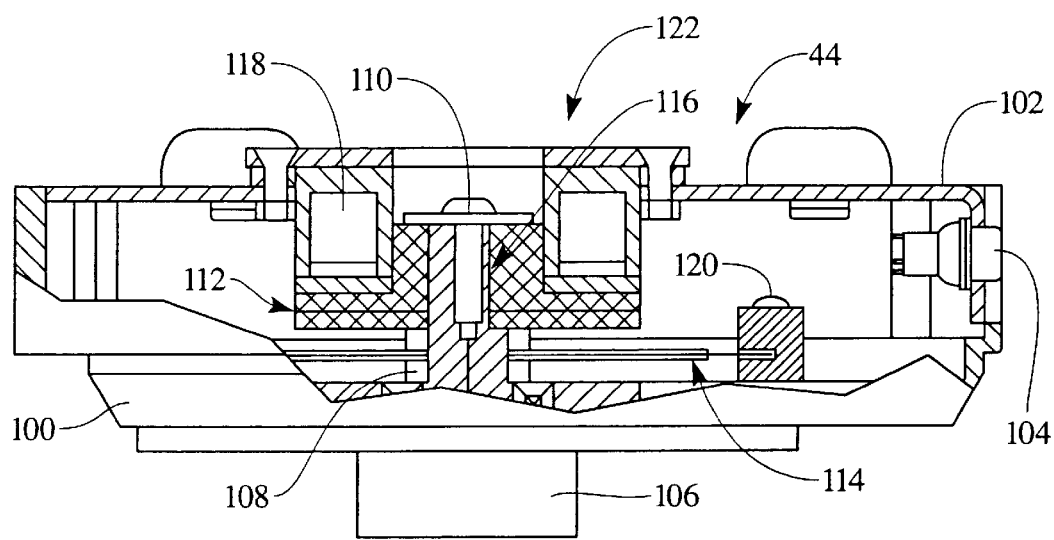
FIG. 4 is a view in cross section of the base joint of the mechanical arm assembly shown in FIG. 2.

With reference now to FIG. 3, an instrument coordinate circuit 72 determines the position and trajectory of the surgical instrument 36 in instrument space, particularly a coordinate system of the instrument. The instrument coordinate circuit includes a guidance device identification circuit 74 and a mechanical arm assembly position circuit 76. The guidance device identification circuit 74 receives the device identification signal from the one or more guidance devices connected to the mechanical arm and indexes a look up table 78 to retrieve dimensional and functional information. The mechanical arm assembly position circuit 76 is connected with the increment resolvers on the mechanical arm assembly 30 to receive signals indicative of changes of position and orientation of the mechanical arm in instrument space. An instrument-planning scanner correlating processor 80 determines the correlation or transform between the surgical instrument 36 and the volumetric scanner 18 coordinate systems. The correlation or transform is normally described in terms of offset, particularly offset along the axis of the patient support, angular offset or rotation, and scaling. In one embodiment, a calibration instrument is touched to a set of spaced apart markers, preferably eight, which are disposed in a known relationship to the volumetric scanner coordinate system. The markers are preferably in the form of a calibration phantom located in the calibration marker area 16. By measuring the coordinates of the calibration instrument in the instrument coordinate system while touching each marker, six or more common points in the two coordinate systems are determined. By determining a barrycenter, centroid, or other characteristic point of the common points, the offset between the two coordinate systems is determined. By determining the angular difference between the rays from the barrycenter to each point in each coordinate system, the angular offset is determined. By determining a difference in physical displacement between the barrycenter and the corresponding points in each coordinate system, the scaling factor is determined. Of course, in a system such as the illustrated embodiment in which the instrument and the volumetric scanner are mechanically linked, the transform or relationship between the volumetric scanner and the instrument coordinate system needs only to be calibrated once and, thereafter, is predetermined from the mechanical interconnection between the component parts. The touching of the markers need only be performed once and subsequently used merely to confirm that the instrument and the CT scanner coordinates have not become misaligned between interventional procedures.

Using analogous mathematics or known mechanical relationships as above, an instrument to patient table correlating processor 82 determines the correlation or transform between the patient table and the surgical instrument. Preferably, the calibration phantom described above having the plurality of markers is positioned in a known position on the table to provide a large number of corresponding points in both coordinate systems for the correlating process. Images of the phantom can be utilized to derive transforms between patient table space and planning or real time image coordinate systems.

Table resolvers 84 located in the patient table contribute vertical and longitudinal offsets to the correlation between the surgical instrument and the patient table when the table is raised or lowered and when the patient support 12 is moved axially. An instrument to patient correlation processor 86 determines a correlation between the surgical instrument system and a patient coordinate system. Preferably, this is done by placing the surgical instrument on three or more known references points on the patient. Such points might include readily identifiable anatomical structures such as the tip of the nose, distinctive points of bones, fiducial markers that are aligned during the volumetric imaging process, or the like.

An instrument to volumetric image coordinate system transform processor 88 receives the correlation or transform from the surgical instrument to planning image processor 80. The instrument to volumetric image processor operates on input position and orientation coordinates in arm space to transform them into volumetric image data space and visa versa. Knowing the position of the surgical instrument in volumetric or planning data space enables the instrument position and orientation to be superimposed on the volumetric planning image data.

During a medical procedure, the patient is positioned in the volumetric planning scanner and a volumetric image is generated. The volumetric image is stored in a volumetric or planning data memory 90. The position of the patient table during the generation of the planning data, particularly as the table moves to generate spiral or slice data, is stored in conjunction with the volumetric planning data such that the data is correlated with the patient table coordinate system. The position of the free end of the arm relative to the patient's body controls the volume planning image data memory or a video processor 92 such that selected slices, projection images, surface renderings, or other conventional displays of the data are generated for display on a planning image display 94. Preferably, the planning image display includes corresponding sagittal coronal axial and oblique slices through a common point of intersection.

Because the planning image display is generated before the surgical procedure, the planning movement of the surgical instrument is preferably displayed in the planning image. The coordinates and trajectory of the surgical instrument are conveyed to the instrument to planning image transform processor 88 for conversion into the planning image coordinate system. The location and trajectory of the instrument in the planning image coordinate system is communicated to the video processor 92 which superimposes the surgical instrument position and trajectory on the CT data display. The position and orientation of this stereotactic arm assembly 30 is communicated to the interventionist control 28, which generates cursor position signals and virtual needle displays that are transformed into the planning image coordinate system 94 and communicated to the video processor 92 to generate a movable cursor point and a virtual needle representation on the planning image display 94. Preferably, the cursor is positioned at the point of intersection of concurrently displayed transverse, coronal, and sagittal views on the volumetric image display 94. As the operator moves the free end of the stereotactic arm assembly through volumetric image data space and as the surgical instrument 36 on the mechanical arm assembly 30 is moved over target areas on the patient, the sagittal, coronal, and transverse views automatically change correspondingly.

FIGS. 4–8 illustrate the brake and encoder assemblies in each of the base, shoulder, elbow, forearm, and wrist joints of the mechanical arm assembly, respectively. With reference now to those FIGURES, but with particular reference first to FIG. 4, the base joint 44 is formed generally of a main body section 100 enclosed on one end by a cover assembly 102. The cover assembly is adapted on one end to receive an electrical connector 104 having a plurality of contact pins for communicating various power, logical, and command signals between the mechanical arm assembly and an arm position and brake controller circuit to be subsequently described below. In the preferred embodiment illustrated, the electrical separates the arm position and brake command signals onto a pair of connectors including an 11 pin Fisher connector and a 4 pin Molex connector.

As is evident from viewing the base joint shown in partial cross section, the cover assembly 102 is adapted to rigidly connect the mechanical arm assembly to the overhead gantry (FIG. 1). The rigid connection between the arm support cover assembly and a bridge mounted on the gantry ensures that cables, wires, or the like extending from the electrical connector will not become twisted or entangled with the mechanical arm as it moves. Various types of cable management systems known in the art may be provided for preventing cable twisting and breakage. The main body section 100 supports a downwardly extending shaft 106 rotatable on precision bearings 108. A button head socket screw 110 fastens a brake armature 112 and an encoder disk 114 to a free end 116 of the shaft 106. As such, the brake armature and encoder disk move as the shaft rotates with respect to the cover assembly connected to the gantry. A brake coil assembly 118 is secured to the cover assembly 102 substantially in a manner as shown. Similarly, an encoder reader 120 is carried on the main body section adjacent an outer end of the encoder disk as shown.

Operationally, as the encoder disk 114 moves relative to the encoder reader 120, a series of pulse signals are generated and supplied to the instrument coordinate circuit 72 (FIG. 3) using suitable electrical connections to the arm position and brake controller circuit. In the preferred embodiment illustrated, the encoder reader is manufactured by immersion and available as Catalog No. 1325. In addition, the electromagnetic brake 122 formed of the coil and armature assemblies described above is available from Electroid under Part No. DC86451. However, in accordance with the present invention, the commercial brake device is selectively modified by using various forms and type of clutch materials and various forms and types of springs to realize the preferred holding forces at each of the arm joints as set forth below.

Further in accordance with the preferred embodiment of the invention, the electromagnetic brake 122 is adapted to lock the shaft 106 in place when electrical power is removed from the coil assembly 118. Upon application of electrical power to the brake coil assembly 118, the brake armature 112 is released from engagement with the coil assembly to enable relative movement between the shaft 106 and the main body portion 100 connected to the overhead support arm 32.

Table I below lists the preferred brake and optical encoder types used for each joint of the mechanical arm according to the present invention.

TABLE I

| Joint | Brake Type | Encoder Type | Holding Force |
|---|---|---|---|
| Base | DC86451 | 3.5", 4096 | 44.2 in-lb |
| Shoulder | DC86456 | 3.5", 4096 | 44.2 in-lb |
| Elbow | Electroid DC86449 | 2", 2048 | 19.5 in-lb |
| Forearm | EFSB-3 | 1", 1024 | 9 in-lb |
| Wrist | Electroid EFSB-1 | 1", 1024 | 3 in.-lb. torque |

Figure 5:
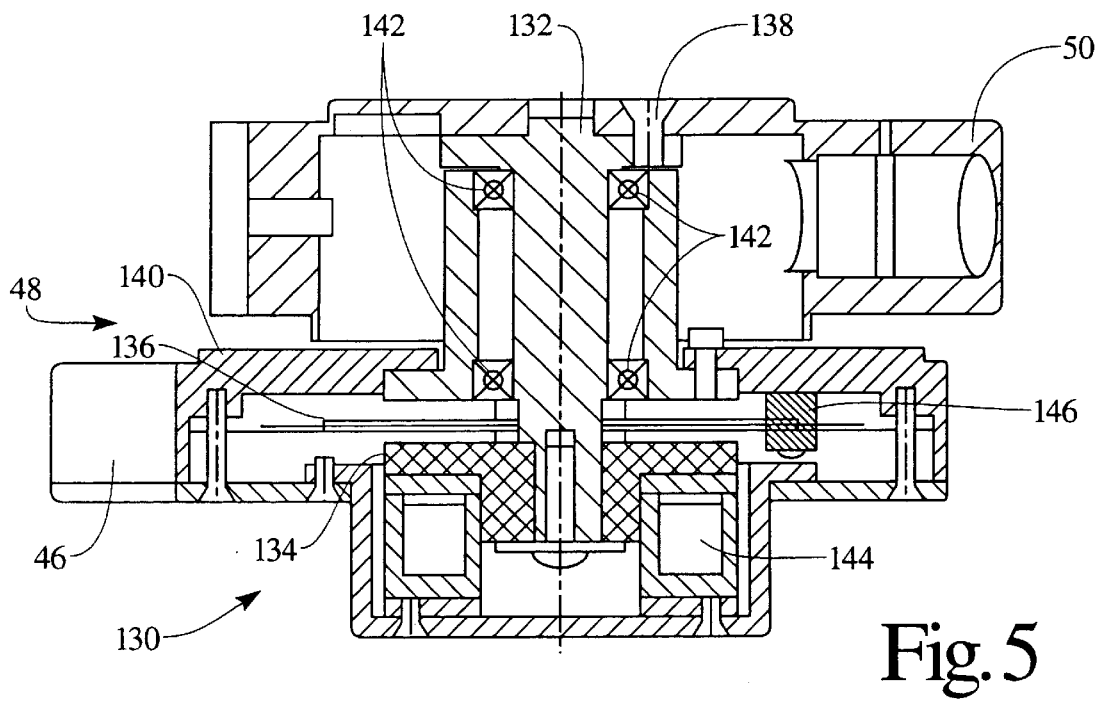
FIG. 5 is a view in cross section of the shoulder joint of the mechanical arm assembly shown in FIG. 2.

Turning next to FIG. 5, a shoulder joint electro-magnetic brake 130 is provided in the shoulder joint 48 between the primary support member 46 and the upper arm member 50. A shaft 132 carries a brake armature 134 and an encoder disk 136. The shaft is connected to the upper arm member 50 using a bolt 138 and is rotatably supported by a shoulder joint base member 140 on precision bearings 142. The brake coil assembly 144 is electrically activated to release and permit free relative movement between the primary support member 46 and the upper arm member 50. An encoder reader 146 is disposed within the base member adjacent the encoder disk 136 in a manner substantially as shown.

Figure 6:
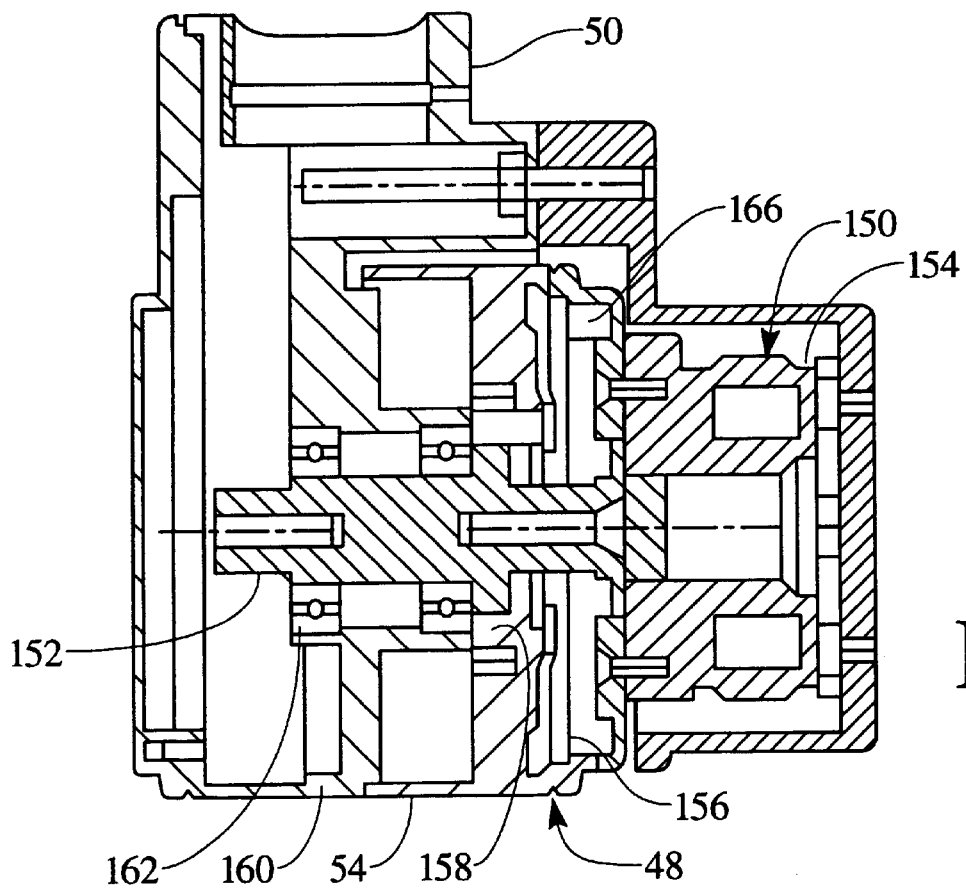
FIG. 6 is a view in cross section of the elbow joint of the mechanical arm assembly shown in FIG. 2.

Turning next to FIG. 6, an elbow electro-magnetic brake 150 is provided in the elbow joint 52 between the upper arm member 50 and the lower arm member 54. A shaft 152 carries a brake armature 154 and an encoder disk 156. The shaft is connected to the upper arm member 50 using a bolt 158 and is rotatably supported by a shoulder joint base member 160 on precision bearings 162. The brake coil assembly 164 is electrically activated to permit free relative movement between the upper arm member 50 and the lower arm member 54. An encoder reader 166 is disposed within the base member adjacent the encoder disk 156 in a manner substantially as shown.

Figure 7:
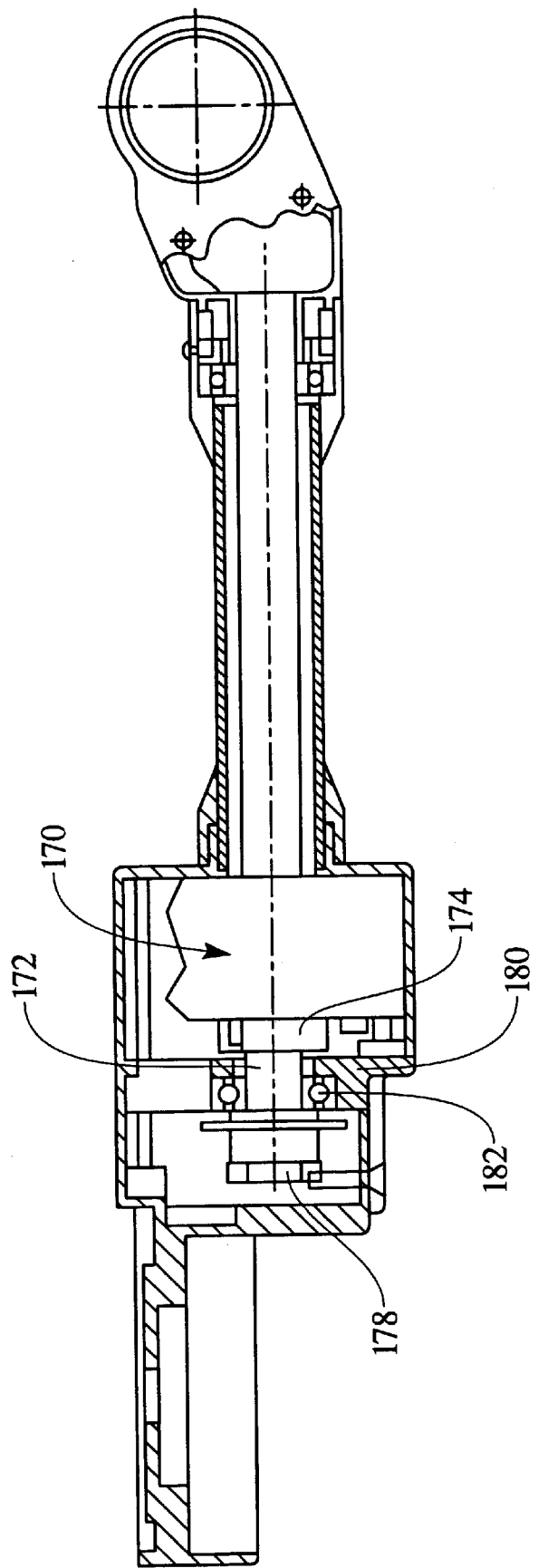
FIG. 7 is a view in cross section of the forearm joint of the mechanical arm assembly shown in FIG. 2.

Turning next to FIG. 7, a forearm electro-mechanical brake 170 is provided in the forearm joint 56 between the lower arm member 54 and the knuckle member 58. A shaft 172 carries a brake armature 174 and an encoder disk 176. The shaft is connected to the lower arm member 54 using a nut 178 and is rotatably supported by a base member 180 on precision bearings 182. The brake coil assembly (not shown) is electrically activated to release and permit free relative movement between the lower arm member 54 and the wrist member 62. An encoder reader (not shown) is disposed within the base member adjacent the encoder disk in a manner well known in the art.

Figure 8:
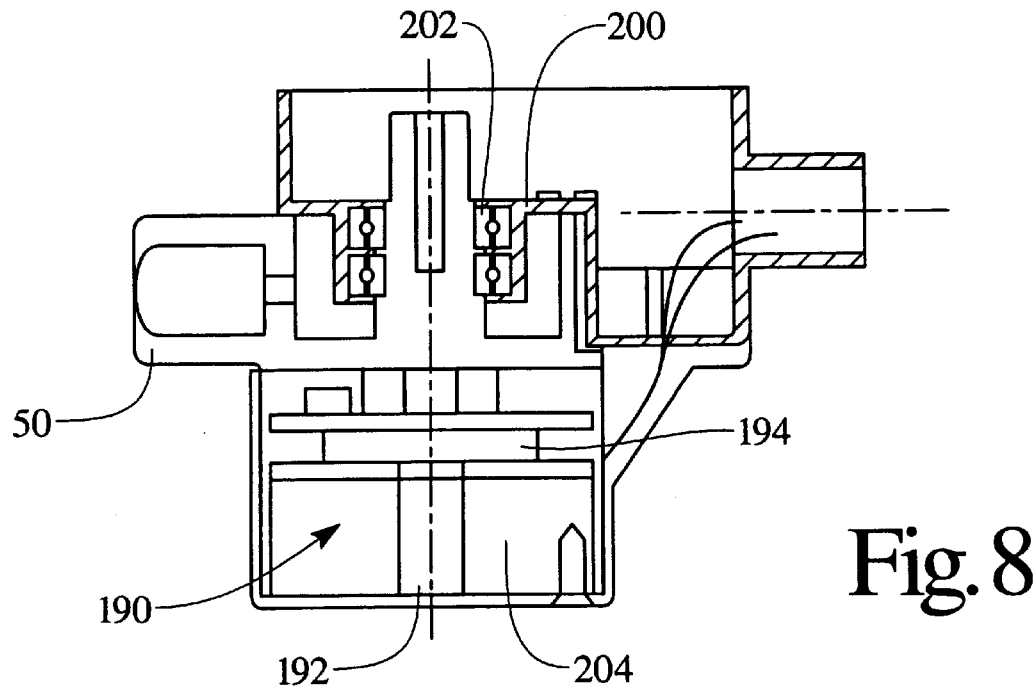
FIG. 8 is a view in cross section of the wrist joint of the mechanical arm assembly shown in FIG. 2.

Turning next to FIG. 8, a wrist electro-mechanical brake 190 is provided in the wrist joint 60 between the knuckle member 58 and the wrist member 62. A shaft 192 carries a brake armature 194 and an encoder disk (not shown). The shaft is connected to the upper arm member 50 using suitable fasteners and is rotatably supported by a wrist joint base member 200 on precision bearings 202. The brake coil assembly 204 is electrically activated to release and permit free relative movement between the knuckle member 58 and the wrist member 62. An encoder reader (not shown) is disposed within the base member adjacent the encoder disk.

Figure 10:
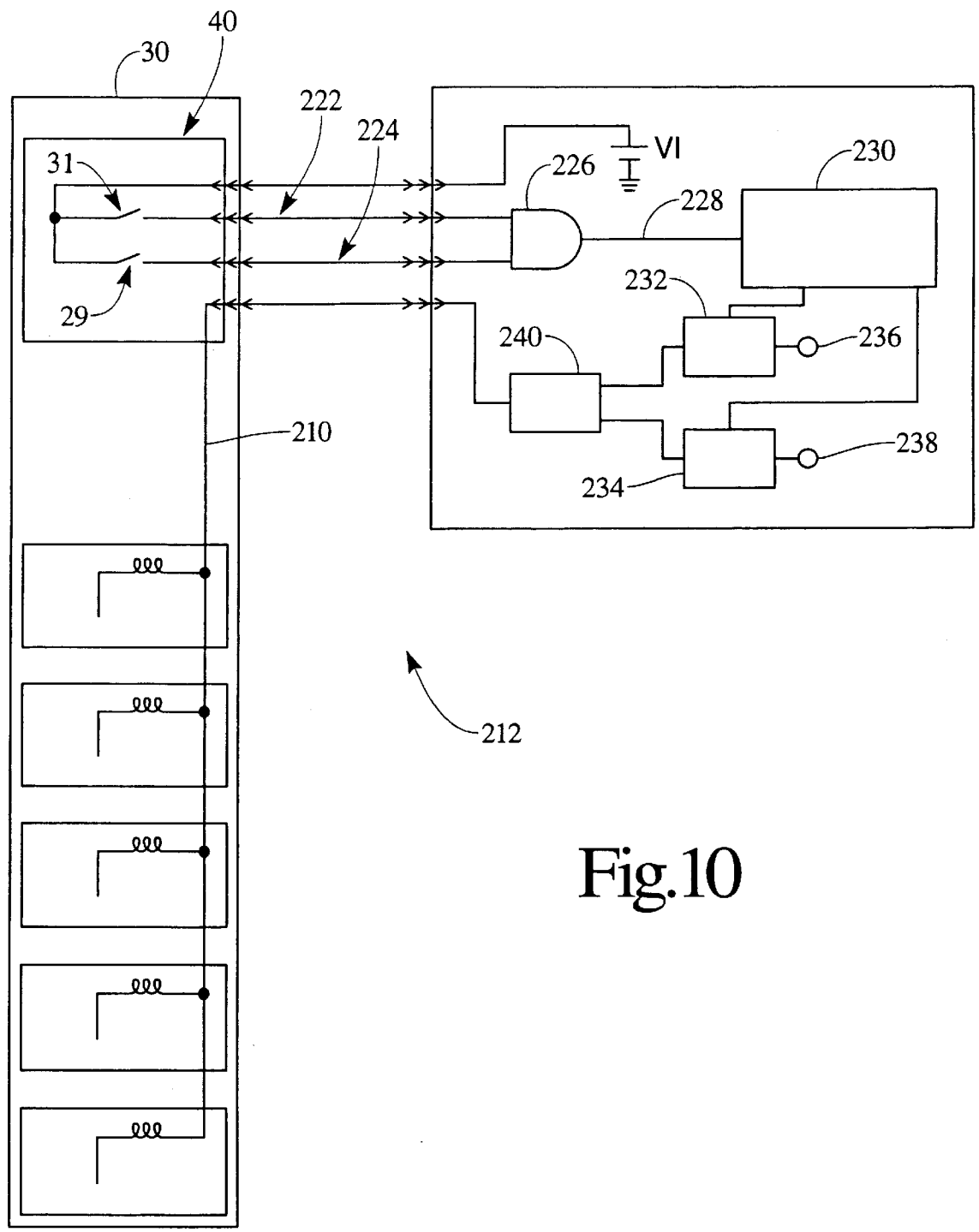

Turning lastly to FIGS. 9 and 10, the brakes described above in the mechanical arm assembly are actuated into a release position by a release command voltage signal 210 generated by a brake controller 212. In an absence of the release command signal 210, the brakes are biased toward a locked or stopped position. In that way, the brakes provide for a fail safe operation of the mechanical arm. Power failures or the like will not cause the arm to release.

In accordance with the preferred embodiment of the instant invention, the release command voltage signal 210 is applied simultaneously to each of the electro-mechanical brakes in a two-step process as shown best in FIG. 9. During a first period 214, a brake unlock signal 216 is applied to each of the brake coil assemblies to separate the brake armatures from engagement with the coil assemblies substantially according to manufacturers' specification. In that regard, the brake unlock signal is preferably a 24 volt DC command signal applied to the brake coil assemblies for a period of one (1) second.

After the first time period, a brake sustain signal 218 is applied to the brake coil assemblies during a second time period 220 for as long as necessary for an interventionist to adjust the arm into a desired position. In accordance with the invention, in order to prevent the brake coil assemblies from overheating and, more importantly, from generating large amounts of heat causing the mechanical arm assembly to deviate from its calibration parameters, the brake sustain signal 218 is at a reduced voltage level, preferably 17 volts.

Turning now more particularly to FIG. 9, the brake controller 210 receives a pair of arm release signals 222, 224 from the pair of membrane switches 29, 31 disposed on the free end 40 of the mechanical arm assembly 30 substantially as described above. The arm release signals are received into an AND circuit 226 which is adapted to generate an arm release initiation signal 228. A processor 230 includes a pair of internal timers for sequentially activating a pair of electronic switches 232, 234 in a manner to connect a first 24 volt voltage source 236 to the brake coil assemblies during the first time period 214. After the expiration of the first time period as determined by the first timer in the processor 230, the second switch 234 is electronically closed and the first switch opened thereby connecting the brake coil assemblies with the second 17 volt source 238.

Lastly, in connection with the brake controller shown in FIG. 9, a low pass filter 240 is used to condition the brake signal so as to substantially eliminate the noise generated during logical transitions of the signal. Without the low pass filter, the noise generated by the brake signal transitions adversely affect the encoder signals. An advantage that flows directly from the low pass filter is the ability to utilize unshielded wires between the brake coil assemblies and the brake controller. This reduces the weight of the mechanical arm assembly and makes it less stiff because smaller wires are more flexible.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A frameless stereotactic surgical apparatus comprising:
   an imaging device for generating first image information regarding a specimen disposed adjacent the imaging device;
   a mechanical arm assembly having a first base portion mounted directly onto the imaging device in a predetermined fixed location on the imaging device, a second free end adapted to move into varied positions near the specimen, and at least one pivot joint between the first base portion and the second free end for permitting selective relative movement between the first base portion and the second free end;
   an electromagnetic brake device adapted to selectively lock the first base portion to the second free end responsive to an electric brake command signal generated by a control circuit operatively associated with the imaging device; and, a transform processor for mapping a position of the free end of the mechanical arm in arm space coordinates to a position in scanner space coordinates, the arm space coordinates relating the mechanical arm assembly to the imaging device and the scanner space coordinates relating the specimen to the imaging device.

2. The frameless stereotactic surgical apparatus according to claim 1 further comprising a position feedback device generating a first joint position signal indicating an orientation of the second free end of the mechanical arm assembly relative to the first base portion.

3. The frameless stereotactic surgical apparatus according to claim 2 wherein:

the first joint position signal is first joint position signal information in said arm space coordinates relating the mechanical arm assembly to the imaging device; and, the first image information is first image information in said scanner space coordinates relating the specimen to the imaging device.

4. The frameless stereotactic surgical apparatus according to claim 1 wherein said imaging device is adapted to generate said electric brake command signal at a first level for a first predetermined time period and generate said electric brake command signal at a second level for a second predetermined time period.

5. The frameless stereotactic surgical apparatus according to claim 1 wherein said electromagnetic brake device is adapted to support said mechanical arm assembly in a predetermined locked position against a force of gravity.

6. The frameless stereotactic surgical apparatus according to claim 5 wherein said electromagnetic brake device is adapted to permit movement of said mechanical arm assembly from said predetermined fixed position against a first offsetting force slightly greater than said force of gravity and against a holding force of said brake device.

7. The frameless stereotactic surgical apparatus according to claim 1 wherein said imaging device includes a low pass filter for filtering high frequency noise components from said electric brake command signal.

8. The frameless stereotactic surgical apparatus according to claim 1 wherein said mechanical arm assembly includes:

a primary support member connected to said first base portion by a base joint;

an upper arm member connected to said primary support member by a shoulder joint;

a lower arm member connected to said upper arm member by an elbow joint;

a knuckle member connected to said lower arm member by a forearm joint; and, a wrist member at said free end of the mechanical arm assembly and connected to said knuckle member by a wrist joint.

9. The frameless stereotactic surgical apparatus according to claim 8 further comprising:

a base joint electromagnetic brake device at said base joint adapted to selectively lock the first base portion to the primary support member responsive to said brake command signal;

a shoulder joint electro-magnetic brake device at said shoulder joint adapted to selectively lock the primary support member to the upper arm member responsive to said brake command signal;

an elbow joint electromagnetic brake device at said elbow joint adapted to selectively lock the upper arm member to the lower arm member responsive to said brake command signal;

a forearm electro-mechanical brake device at said forearm joint adapted to selectively lock the lower arm member to the knuckle member responsive to said brake command signal; and, a wrist electromechanical brake device at said wrist joint adapted to selectively lock the knuckle member to the wrist member responsive to said brake command signal.

10. The frameless stereotactic surgical apparatus according to claim 9 wherein:

the base joint electro-magnetic brake device has a holding force of 44.2 in-lb;

the shoulder joint electromagnetic brake device has a holding force of 44.2 in-lb;

the elbow joint electro-magnetic brake device has a holding force of 19.5 in-lb;

the forearm joint electro-mechanical brake device has a holding force of 9 in-lb; and, the wrist joint electro-mechanical brake device has a holding force of 3 in-lb.

11. The frameless stereotactic surgical apparatus according to claim 1 wherein the first base portion of said mechanical arm assembly is mounted directly onto the imaging device in a one of a plurality of predetermined fixed locations on the imaging device.

12. A method of using a surgical instrument guide apparatus with a stereotactic imaging device adapted to receive a patient or a patient support table, the method comprising the steps of:

registering the surgical instrument guide apparatus with the stereotactic imaging device by mechanically connecting a base end of the guide apparatus directly to the imaging device;

using the imaging device, generating a first image information in scanner space coordinates regarding a patient disposed on the patient support table;

generating guide tip position information in guide space coordinates indicating a position of a free end of the guide apparatus relative to said base end of the guide apparatus;

using a transform processor in the imaging device, mapping the guide tip position information in said guide space coordinates to guide tip position information in said scanner space coordinates to relate the guide apparatus to the imaging device;

using the transform processor in the imaging device, mapping the first image information and the guide tip position information in said scanner space coordinates to image space coordinates adapted for display on a human readable display monitor; and, displaying on a human readable display monitor said first image information in said image space coordinates together with said guide tip position information in said image space coordinates to present a human interventionist with a visual representation of the surgical instrument guide apparatus together with an image of the patient on the patient support table.

13. The method of using a surgical instrument guide apparatus with a stereotactic imaging device according to claim 12 wherein the step of registering the surgical instrument guide apparatus with the stereotactic imaging device includes mechanically connecting said base end of the guide apparatus directly to the imaging device at a one of a plurality of predetermined fixed locations on the imaging device.

14. The method of using a surgical instrument guide apparatus with a stereotactic imaging device according to claim 12 further including the step of providing an electromagnetic brake in said surgical instrument guide apparatus, the electromagnetic brake device being adapted to selectively lock the free end relative to the base end in response to an electric brake command signal generated by a control circuit operatively associated with the imaging device, the electromagnetic brake device being adapted to selectively support said surgical instrument guide apparatus in a predetermined locked position against a force of gravity and being adapted to permit movement of said surgical instrument guide apparatus from said predetermined fixed position against a first offsetting force slightly greater than said force of gravity and against a holding force of said electromagnetic brake.

15. A frameless stereotactic surgical apparatus comprising:

an imaging device for generating first image information regarding a specimen disposed adjacent the imaging device;

a mechanical arm assembly having a first base portion mounted directly onto the imaging device in a predetermined fixed position on the imaging device, a second free end adapted to move into varied positions near the specimen, and at least one pivot joint between the first base portion and the second free end for permitting selective relative movement between the first base portion and the second free end;

an electromagnetic brake device for selectively locking the first base portion to the second free end responsive to an electric brake command signal generated by a control circuit operatively associated with the imaging device, the electromagnetic brake device being adapted to support said mechanical arm assembly in a predetermined locked position against a force of gravity and to permit movement of said mechanical arm assembly from said predetermined fixed position against a first offsetting force slightly greater than said force of gravity and against a holding force of said brake devices and, a transform processor for mapping a location of the free end of the mechanical arm in arm space coordinates relating the mechanical arm assembly relative to the imaging device to a location in scanner space coordinates relating a position of said specimen relative to the imaging device.

16. The frameless stereotactic surgical apparatus according to claim 15 wherein said imaging device is adapted to generate said electric brake command signal at a first level for a first predetermined time period to separate a brake armature from engagement with a brake coil and generate said electric brake command signal at a second level for a second predetermined time period to sustain the brake armature separated from engagement with the brake coil.

17. The frameless stereotactic surgical apparatus according to claim 15 further comprising a position feedback device generating a first joint position signal indicating an orientation of the second free end of the mechanical arm assembly relative to the first base portion.

18. The frameless stereotactic surgical apparatus according to claim 17 wherein:

the first joint position signal is first joint position signal information in said arm space coordinates relating the mechanical arm assembly to the imaging device; and, the first image information is first image information in said scanner space coordinates relating the specimen to the imaging device.

19. A frameless stereotactic surgical apparatus comprising:

an imaging device for generating first image information regarding a specimen disposed adjacent the imaging device;

a mechanical arm assembly having a first base portion mounted directly onto the imaging device in a predetermined fixed location on the imaging device, a second free end adapted to move into varied positions near the specimen, and at least one pivot joint between the first base portion and the second free end for permitting selective relative movement between the first base portion and the second free end;

an electromagnetic brake device adapted to selectively lock the first base portion to the second free end responsive to an electric brake command signal generated by a control circuit operatively associated with the imaging device;

a low pass filter for filtering high frequency noise components from said electric brake command signal; and, a transform processor for mapping a position of the free end of the mechanical arm assembly in arm space coordinates relating the mechanical arm assembly to the imaging device to a position in scanner space coordinates relating the specimen to the imaging device.

20. The frameless stereotactic surgical apparatus according to claim 19 wherein the electromagnetic brake device is adapted to support said mechanical arm assembly in a predetermined locked position against a force of gravity and to permit movement of said mechanical arm assembly from said predetermined fixed position against a first offsetting force slightly greater than said force of gravity and against a holding force of said electromagnetic brake device.

21. The frameless stereotactic surgical apparatus according to claim 19 wherein said imaging device is adapted to generate said electric brake command signal at a first level for a first predetermined time period to separate a brake armature from engagement with a brake coil and generate said electric brake command signal at a second level for a second predetermined time period to sustain the brake armature separated from engagement with the brake coil.

22. The frameless stereotactic surgical apparatus according to claim 19 further comprising a position feedback device generating a first joint position signal indicating an orientation of the second free end of the mechanical arm assembly relative to the first base portion.

23. The frameless stereotactic surgical apparatus according to claim 22 wherein:

the first joint position signal is first joint position signal information in said arm space coordinates relating the mechanical arm assembly to the imaging device; and, the first image information is first image information in said scanner space coordinates relating the specimen to the imaging device.

* * * * *